United States Patent
Freeman et al.

(10) Patent No.: US 10,013,708 B1
(45) Date of Patent: Jul. 3, 2018

(54) ESTIMATING A CONDITION OF A PHYSICAL STRUCTURE

(71) Applicant: STATE FARM MUTUAL AUTOMOBILE INSURANCE COMPANY, Bloomington, IL (US)

(72) Inventors: James M. Freeman, Normal, IL (US); Roger D. Schmidgall, Normal, IL (US); Patrick H. Boyer, Bloomington, IL (US); Nicholas U. Christopulos, Bloomington, IL (US); Jonathan D. Maurer, Bloomington, IL (US); Nathan L. Tofte, Downs, IL (US); Jackie O. Jordan, II, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 184 days.

(21) Appl. No.: 14/968,147

(22) Filed: Dec. 14, 2015

Related U.S. Application Data

(63) Continuation of application No. 14/496,802, filed on Sep. 25, 2014, now Pat. No. 9,262,788, which is a continuation of application No. 13/836,695, filed on Mar. 15, 2013, now Pat. No. 8,872,818.

(51) Int. Cl.
*G06Q 40/00* (2012.01)
*G06T 17/00* (2006.01)
*G06Q 30/02* (2012.01)
*G01N 22/02* (2006.01)
*G01N 21/88* (2006.01)
*G06Q 50/16* (2012.01)
*G06Q 40/08* (2012.01)
*G06T 17/20* (2006.01)

(52) U.S. Cl.
CPC ..... *G06Q 30/0278* (2013.01); *G01N 21/8851* (2013.01); *G01N 22/02* (2013.01); *G06Q 40/08* (2013.01); *G06Q 50/163* (2013.01); *G06T 17/20* (2013.01); *G06T 2207/10032* (2013.01)

(58) Field of Classification Search
None
See application file for complete search history.

(56) References Cited

U.S. PATENT DOCUMENTS

| | | | |
|---|---|---|---|
| 5,304,809 | A | 4/1994 | Wickersheim |
| 5,697,001 | A | 12/1997 | Ring et al. |
| 5,950,169 | A | 9/1999 | Borghesi et al. |
| 6,181,837 | B1 | 1/2001 | Cahill et al. |

(Continued)

OTHER PUBLICATIONS

Ku, Abdil. "Implementation of 3D Optical Scanning Technology for Automotive Applications." Sensors (Basel, Switzerland) 9.3 (2009): 1967-1979. PMC. Web. Nov. 10, 2017.*

(Continued)

*Primary Examiner* — Utpal Shah
(74) *Attorney, Agent, or Firm* — Marshall, Gerstein & Borun LLP

(57) ABSTRACT

In a computer-implemented method and system for capturing the condition of a structure, the structure is scanned with a three-dimensional (3D) scanner. The 3D scanner generates 3D data. A point cloud or 3D model is constructed from the 3D data. The point cloud or 3D model is then analyzed to determine the condition of the structure.

13 Claims, 6 Drawing Sheets

(56) References Cited

U.S. PATENT DOCUMENTS

| | | |
|---|---|---|
| 6,574,377 B1 | 6/2003 | Cahill et al. |
| 7,130,066 B1 | 10/2006 | Kanematu |
| 7,343,307 B1 | 3/2008 | Childress |
| 7,752,286 B2 | 7/2010 | Anderson et al. |
| 7,809,587 B2 | 10/2010 | Dorai et al. |
| 7,885,829 B2 | 2/2011 | Danico et al. |
| 7,889,931 B2 | 2/2011 | Webb et al. |
| 7,953,615 B2 | 5/2011 | Aquila et al. |
| 7,984,500 B1 | 7/2011 | Khanna et al. |
| 8,265,963 B1 | 9/2012 | Hanson et al. |
| 8,284,194 B2 | 10/2012 | Zhang et al. |
| 8,370,373 B2 | 2/2013 | Yamamoto |
| 8,374,957 B1 | 2/2013 | Garcia et al. |
| 8,401,879 B1 | 3/2013 | Kazenas |
| 8,510,196 B1 | 8/2013 | Brandmaier et al. |
| 8,527,305 B1 | 9/2013 | Hanson et al. |
| 8,537,338 B1 | 9/2013 | Medasani et al. |
| 8,543,486 B2 | 9/2013 | Donoho et al. |
| 8,651,206 B2 | 2/2014 | Slawinski et al. |
| 8,756,085 B1 | 6/2014 | Plummer et al. |
| 8,818,572 B1 | 8/2014 | Tofte et al. |
| 8,861,808 B2 | 10/2014 | Kulcke et al. |
| 8,872,818 B2 | 10/2014 | Freeman et al. |
| 8,874,454 B2 | 10/2014 | Plummer et al. |
| 8,931,144 B2 | 1/2015 | Freeman et al. |
| 9,002,719 B2 | 4/2015 | Tofte |
| 9,082,015 B2 | 7/2015 | Christopulos et al. |
| 9,098,655 B2 | 8/2015 | Plummer et al. |
| 9,131,224 B1 | 9/2015 | Freeman et al. |
| 2002/0030142 A1 | 3/2002 | James |
| 2002/0055861 A1 | 5/2002 | King et al. |
| 2002/0060267 A1 | 5/2002 | Yavnai |
| 2003/0067461 A1 | 4/2003 | Fletcher et al. |
| 2003/0154111 A1 | 8/2003 | Dutra et al. |
| 2003/0200123 A1 | 10/2003 | Burge et al. |
| 2003/0212478 A1 | 11/2003 | Rios |
| 2005/0007633 A1 | 1/2005 | Kadowaki |
| 2005/0108065 A1 | 5/2005 | Dorfstatter |
| 2005/0144189 A1 | 6/2005 | Edwards et al. |
| 2005/0165517 A1 | 7/2005 | Reich |
| 2005/0276401 A1 | 12/2005 | Madill et al. |
| 2006/0031103 A1 | 2/2006 | Henry |
| 2007/0050360 A1 | 3/2007 | Hull et al. |
| 2007/0091320 A1* | 4/2007 | Hu .................... G01B 11/2513 356/604 |
| 2007/0179868 A1 | 8/2007 | Bozym |
| 2008/0174789 A1 | 7/2008 | Uffenkamp et al. |
| 2009/0028003 A1 | 1/2009 | Behm et al. |
| 2009/0055226 A1 | 2/2009 | Tritz et al. |
| 2009/0119132 A1 | 5/2009 | Bolano et al. |
| 2009/0138290 A1 | 5/2009 | Holden |
| 2009/0148068 A1 | 6/2009 | Woodbeck |
| 2009/0265193 A1* | 10/2009 | Collins .............. G06Q 30/0185 705/4 |
| 2010/0094664 A1 | 4/2010 | Bush et al. |
| 2010/0104191 A1 | 4/2010 | McGwire |
| 2010/0111370 A1 | 5/2010 | Black et al. |
| 2010/0161155 A1 | 6/2010 | Simeray |
| 2010/0228406 A1 | 9/2010 | Hamke et al. |
| 2010/0231692 A1 | 9/2010 | Perlman et al. |
| 2010/0292871 A1 | 11/2010 | Schultz et al. |
| 2010/0302359 A1 | 12/2010 | Adams et al. |
| 2011/0049290 A1 | 3/2011 | Seydoux et al. |
| 2011/0187713 A1 | 8/2011 | Pershing et al. |
| 2011/0302091 A1 | 12/2011 | Hornedo |
| 2012/0004793 A1 | 1/2012 | Block |
| 2012/0013617 A1 | 1/2012 | Zhang et al. |
| 2012/0076437 A1 | 3/2012 | King |
| 2012/0179431 A1 | 7/2012 | Labrie et al. |
| 2012/0303179 A1 | 11/2012 | Schempf |
| 2013/0051639 A1 | 2/2013 | Woodford et al. |
| 2013/0233964 A1 | 9/2013 | Woodworth et al. |
| 2013/0262153 A1 | 10/2013 | Collins et al. |
| 2013/0321393 A1 | 12/2013 | Winder |
| 2014/0163775 A1 | 6/2014 | Metzler |
| 2014/0168420 A1 | 6/2014 | Naderhirn et al. |
| 2014/0226182 A1 | 8/2014 | Lee et al. |
| 2014/0245165 A1 | 8/2014 | Battcher et al. |
| 2014/0278587 A1 | 9/2014 | Plummer et al. |
| 2014/0297065 A1 | 10/2014 | Tofte et al. |
| 2014/0324483 A1 | 10/2014 | Plummer et al. |
| 2015/0348253 A1* | 12/2015 | Bendall ................. G06T 7/0004 348/86 |
| 2016/0078610 A1* | 3/2016 | Rudd .................... G06T 7/0004 348/87 |
| 2016/0102966 A1* | 4/2016 | Grossnickle .......... B29C 70/382 356/630 |
| 2016/0169665 A1* | 6/2016 | Deschenes ......... G01N 21/8806 356/606 |
| 2016/0259038 A1* | 9/2016 | Retterath .............. G01S 7/4802 |
| 2016/0300003 A1* | 10/2016 | Knoll .................. G06F 17/5018 |

OTHER PUBLICATIONS

Cost Containment, Product and Solutions for the Property and Casualty Insurance Industry, Computer Sciences Corporation (1999).

Final Office Action, U.S. Appl. No. 13/647,098, dated Nov. 1, 2013.

Final Office Action, U.S. Appl. No. 13/647,098, dated Oct. 9, 2014.

Final Office Action, U.S. Appl. No. 13/836,695, dated Feb. 25, 2014.

Final Office Action, U.S. Appl. No. 13/839,634, dated Mar. 21, 2014.

Final Office Action, U.S. Appl. No. 13/839,634, dated Dec. 2, 2014.

Final Office Action, U.S. Appl. No. 14/269,920, dated Feb. 11, 2015.

Final Office Action, U.S. Appl. No. 14/323,626, dated Apr. 3, 2015.

Final Office Action, U.S. Appl. No. 14/496,802, dated May 4, 2015.

Final Office Action, U.S. Appl. No. 14/496,840, dated May 5, 2015.

Foo et al., Three-dimensional path planning of unmanned aerial vehicles using particle swarm optimization, Sep. 2006, AIAA.

Kluckner et al., Image based building classification and 3D modeling with super-pixels, ISPRS Technical Commission II Symposium, PCV 2010, vol. XXXVIII, part 3A, pp. 233-8 (Sep. 3, 2010).

Merz et al., Beyond Visual Range Obstacle Avoidance and Infrastructure Inspection by an Autonomous Helicopter, Sep. 2011, IEEE.

Nonfinal Office Action, U.S. Appl. No. 13/647,098, dated Apr. 26, 2013.

Nonfinal Office Action, U.S. Appl. No. 13/647,098, dated Mar. 14, 2014.

Nonfinal Office Action, U.S. Appl. No. 13/836,695, dated Oct. 3, 2013.

Nonfinal Office Action, U.S. Appl. No. 13/839,634, dated Aug. 5, 2014.

Nonfinal Office Action, U.S. Appl. No. 13/839,634, dated Oct. 25, 2013.

Nonfinal Office Action, U.S. Appl. No. 14/269,920, dated Jul. 13, 2015.

Nonfinal Office Action, U.S. Appl. No. 14/269,920, dated Sep. 25, 2014.

Nonfinal Office Action, U.S. Appl. No. 14/318,521, dated Oct. 10, 2014.

Nonfinal Office Action, U.S. Appl. No. 14/323,626, dated Sep. 17, 2014.

Nonfinal Office Action, U.S. Appl. No. 14/496,802, dated Jan. 2, 2015.

Nonfinal Office Action, U.S. Appl. No. 14/496,840, dated Jan. 5, 2015.

Nonfinal Office Action, U.S. Appl. No. 14/631,568, dated May 19, 2015.

Nonfinal Office Action, U.S. Appl. No. 14/656,185, dated Apr. 2, 2015.

Nonfinal Office Action, U.S. Appl. No. 14/820,328, dated Sep. 24, 2015.

Notice of Allowance, U.S. Appl. No. 13/647,098, dated Dec. 10, 2014.

Notice of Allowance, U.S. Appl. No. 13/836,695, dated Jun. 27, 2014.

(56) References Cited

OTHER PUBLICATIONS

Notice of Allowance, U.S. Appl. No. 13/839,634, dated Mar. 13, 2015.
Notice of Allowance, U.S. Appl. No. 14/318,521, dated Apr. 10, 2015.
UTC Spotlight: Superstorm Sandy LiDAR Damage Assessment to Change Disaster Recovery, Feb. 2013.
Woodbeck et al., "Visual cortex on the GPU: Biologically inspired classifier and feature descriptor for rapid recognition," IEEE Computer Society Conference on Computer Vision and Pattern Recognition Workshops 2008, pp. 1-8 (2008).

* cited by examiner

ESTIMATING A CONDITION OF A PHYSICAL STRUCTURE

CROSS-REFERENCE TO RELATED APPLICATIONS

This application is a continuation of U.S. application Ser. No. 14/496,802, filed Sep. 25, 2014 and titled "Methods and Systems for Capturing the Condition of a Physical Structure via Detection of Electromagnetic Radiation," which is a continuation of U.S. application Ser. No. 13/836,695, filed Mar. 15, 2013 and titled "Methods and Systems for Capturing the Condition of a Physical Structure," the disclosures of which are expressly incorporated herein by reference.

TECHNICAL FIELD

This disclosure relates to 3D modeling, and in particular, to estimating the condition of a structure using 3D modeling.

BACKGROUND

The present disclosure generally relates to a system or method for inspecting a structure to estimate the condition of the structure. After an accident or loss, property owners typically file claims with their insurance companies. In response to these claims, the insurance companies assign an appraiser to investigate the claims to determine the extent of damage and/or loss, document the damage, and provide its clients with appropriate compensation.

Determining and documenting the extent of damage can be risky for the appraiser. For example, in a situation where a structure has experienced roof damage, appraisers typically climb onto the roof to evaluate the damage. Once on the roof they may sketch the damaged area of the roof in order to document the damage. In the alternative, appraisers might take a digital picture of the damaged area. In either scenario, the appraise has exposed himself to a risk of falling. Afterwards, the picture is typically attached to an electronic claim file for future reference where it can be analyzed by an appraiser to estimate the extent of damage to the structure.

The process for determining and documenting the extent of the damage can be inefficient and time consuming. In addition to the time required to drive to and from the incident site and to perform the inspection itself, significant paperwork and calculations may be involved in calculating compensation owed to the clients. For example, if an insurance appraiser takes photos on the roof of a client's building to assess a claim for roof damage from a hurricane, in order to calculate how much money should be paid to the client, the appraiser may have to come back to his office, research the client's property, research the cost of the damaged property and research repair costs. All of these steps are time consuming and both delay payment to the client and prevent the appraiser from assessing other client claims.

In situations where the insurance company has received a large number of claims in a short time period (e.g., when a town is affected by a hurricane, tornado, or other natural disaster), an insurance appraiser may not have time to perform a timely claim investigations of all the received claims. If claim investigations are not performed quickly, property owners may not receive recovery for their losses for long periods of time. Additionally, long time delays when performing claim investigations can lead to inaccurate investigations results (e.g., the delay may lead to increased opportunity for fraud and/or may make it more difficult to ascertain the extent of damage at the time of the accident or loss).

Finally, two-dimensional digital pictures or video of a roof or structure often provide inadequate detail for thorough inspection of a structure. Poor image quality resulting from camera movement or out-of-focus images can make it difficult to estimate the condition of a property based on an image. Even where image quality is adequate, poor angles or bad lighting may hide or exaggerate details important to estimating the condition of the structure, leading to inaccurate assessments of the structure's condition.

SUMMARY

A system and method for inspecting a structure and estimating the condition of the structure includes deploying one or more 3D scanners to scan a structure and generating, at the one or more 3D scanners, a plurality of 3D data points corresponding to points on the surface of the structure. The method further includes identifying coordinate sets, at the one or more 3D scanners, associated with each of the generated plurality of 3D data points. The method also includes storing a point cloud, comprising one or more of the generated plurality of 3D data points, to a memory. The method further includes causing a processor to construct a 3D model from the point cloud and storing the 3D model to the memory. Then, the processor analyzes the 3D model to identify features associated with the structure. The processor finally generates an estimate of the condition of the structure based on the identified features before storing the estimate to memory. In some embodiments the estimate of the condition of the structure may be used to calculate a financial cost estimate (representing, for example, a loss in value or a cost to repair damage).

The 3D scanners may be contact 3D scanners (detecting 3D information via physical contact with a structure) or non-contact 3D scanners (detecting 3D information via light or sound, for example, reflected off of the structure). In some embodiments, the contact 3D scanner detects 3D information by using a tactile sensor to detect an imprint left on a pad that was stamped on the surface or a roller that was rolled across the surface. In other embodiments, the contact scanner detects 3D information by pulling, tapping or scraping objects on the structure (such as roof shingles). In some instances the 3D scanner utilizes an audio sensor to listen for an audio response to the tapping.

The non-contact 3D scanners may detect sound or electromagnetic radiation (including white light, laser light, infrared light, ultraviolet light) to generate the 3D data points. The 3D scanner may identify coordinate sets associated with the 3D data points by detecting a projected light pattern or laser using triangulation methods or time-of-flight methods (timing how long it takes for a light to reflect off of a surface). The 3D scanners may also generate 3D data points by detecting a chemical sprayed onto the structure (wherein the chemical may pool in cracks or crevices, for example).

The 3D scanners may be physically connected to (or may themselves be) stationary devices, flying devices, hovering devices, crawling devices or rolling devices. The 3D scanners may also be physically connected to (or may themselves be) a wirelessly controlled device or an autonomously controlled device.

In some instances, the processor that analyzes the 3D model to identify features associated with the structure is located in a data analysis system remotely located relative to the 3D scanners. In other instances, the processor that analyzes the 3D model may be in a system in close proximity to the 3D scanners.

DETAILED DESCRIPTION

Figure 1A:
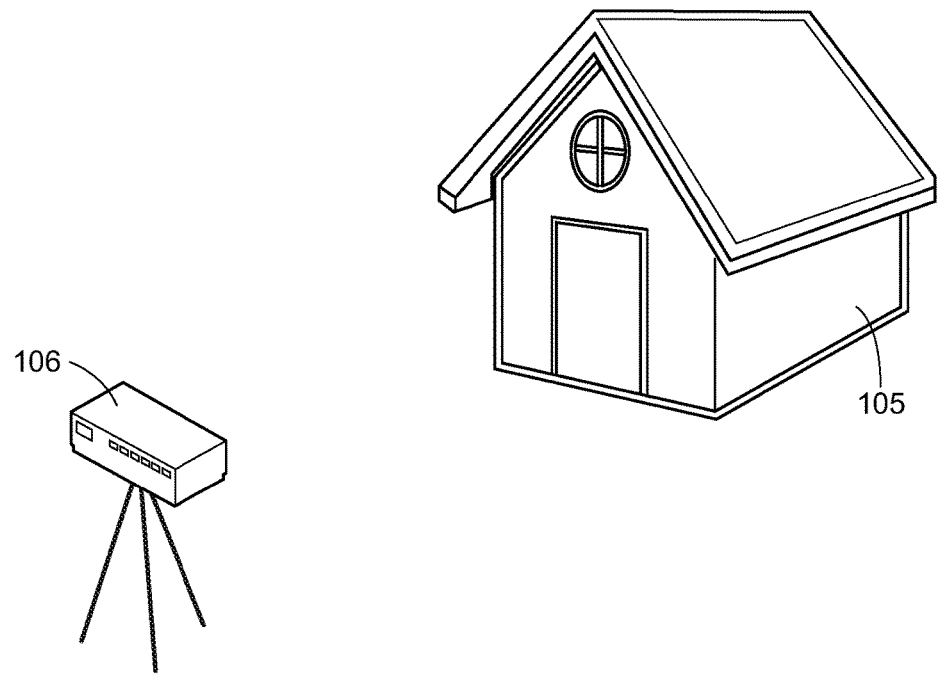
FIG. 1a illustrates a block diagram of a property inspection system according to an embodiment of the present disclosure.

FIG. 1a illustrates a block diagram of a property inspection system 106 according to an exemplary embodiment. The property inspection system 106 is configured to inspect the structure 105. The structure 105 may be any type of construction or object. In certain embodiments, the structure 105 may be a building, which may be residential, commercial, industrial, agricultural, educational, or of any other nature. In other embodiments the structure 105 may be personal property such as a vehicle, boat, aircraft, furniture, etc. The property inspection system 106 may include a number of modules, devices, systems, sub-systems, or routines. For example, the property inspection system 106 includes a 3D scanning system or 3D scanner for generating 3D data, and may include a number of other sensing devices. In some embodiments, the property inspection system 106 includes a data collection module or system (for scanning or collecting the structure 105) and a data analysis module or system (for analyzing the scanned or collected data). The property inspection system 106 may be utilized in a number of situations, but in the preferred embodiment, a user associated with an insurance company utilizes the property inspection system 106 for the purpose of estimating the condition of the structure 105. In one embodiment, an insurance policy-holder may file a claim because the policyholder believes that the structure 105 is damaged. A user (e.g., an insurance company or claim adjuster) may then deploy the property inspection system 106 to inspect the structure 105 and estimate the condition of the structure 105. In other embodiments, the user may be an appraiser appraising the structure 105 or an inspector inspecting the structure 105.

In operation, the property inspection system 106 inspects the structure 105 by scanning the structure 105 to detect information related to the structure 105. The information may relate to any kind of audio, visual, tactile or thermal features associated with the structure 105. The property inspection system 106 uses the detected information to generate data representative of one or more features associated with the structure 105. For example, and as further described below, the property inspection system 106 may scan the structure 105 and generate a full-color 3D model of the structure 105. The property inspection system 106 then analyzes the data to estimate the condition of the structure 105. Based on the estimated condition of the structure, the property inspection system 106 may also determine that the structure 105 is damaged and may then automatically calculate a financial cost associated with the damage. For example, the property inspection system 106 may determine that the roof of the structure 105 is damaged and then calculate how much it will cost to fix the roof. With regard to a vehicle, boat, or aircraft, the property inspection system 106 may determine that a body panel, window, frame, or another surface associated with the vehicle, boat, or aircraft is damaged. The property inspection system 106 may calculate a cost to fix the body panel, window, frame, or other surface.

Figure 1B:
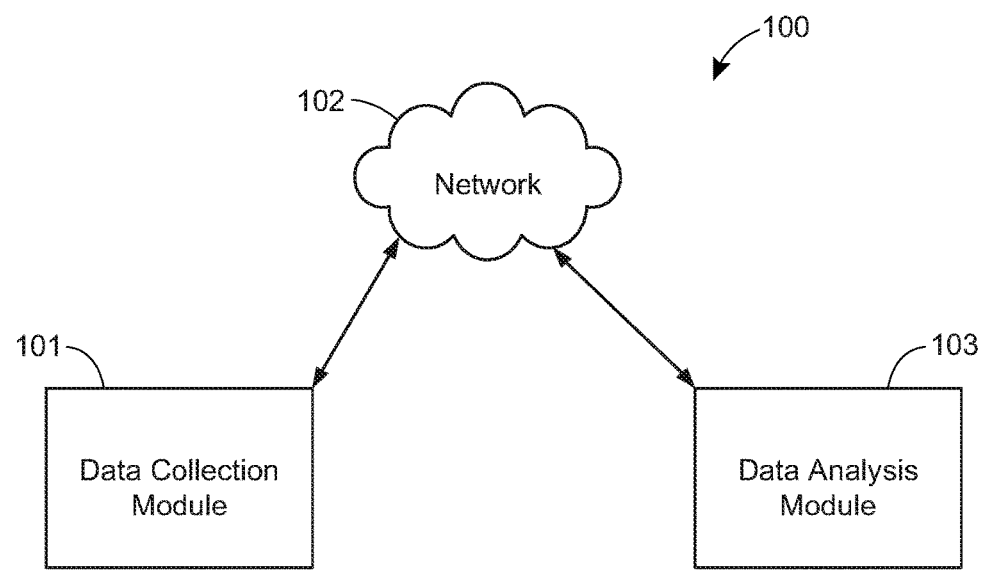
FIG. 1b illustrates a block diagram of a property inspection system according to a further embodiment of the present disclosure

FIG. 1b illustrates a block diagram of a property inspection system 100 according to a further embodiment of the present disclosure. The property inspection system 100 includes a data collection module 101, a network 102, and a data analysis module 103. In the property inspection system 100, the data collection module 101 and the data analysis module 103 are each communicatively connected to the network 102. In alternative embodiments of the property inspection system 100, the data collection module 101 may be in direct wired or wireless communication with the data analysis module 103. Furthermore, in some embodiments the data collection module 101 and the data analysis module 103 may exist on a single device or platform and may share components, hardware, equipment, or any other resources. The network 102 may be a single network, or may include multiple networks of one or more types (e.g., a public switched telephone network (PSTN), a cellular telephone network, a wireless local area network (WLAN), the Internet, etc.).

In operation of the property inspection system 100, the data collection module 101 scans a structure (such as structure 105) and generates data representing the scanned information. In certain embodiments, the data collection module is operable on a 3D scanning system such as the data collection system 201 shown in FIG. 2. The generated data may represent a point cloud or 3D model of the scanned structure. The data collection module 101 transmits the generated data over the network 102. The data analysis module 103 receives the generated data from the network 102, where the data analysis module 103 operates to estimate the condition of the structure by analyzing the generated data. In some embodiments, estimating the condition of the structure may include comparing the generated data to reference data. The reference data may be any type of data that can provide a point of comparison for estimating the condition of the structure. For example, the reference data may represent an image, model, or any previously collected or generated data relating to the same or a similar structure. The reference data may also represent stock images or models unrelated to the scanned structure. Furthermore, the data analysis module 103 may use the estimate of the condition of the structure to determine that the structure is damaged, and then may calculate an estimated cost correlated to the extent of the damage to the structure.

In some embodiments of the property inspection system 100, the data collection module 101 wirelessly transmits, and the data analysis module 103 wirelessly receives, the generated data. While in the preferred embodiment the generated data represents a point cloud or 3D model of the scanned structure, the generated data may also correspond to any visual (2D or 3D), acoustic, thermal, or tactile characteristics of the scanned structure. The data collection module 101 may use one or more 3D scanners, image sensors, video recorders, light projectors, audio sensors, audio projectors, chemical sprays, chemical sensors, thermal sensors, or tactile sensors to scan the structure and generate the data. In some embodiments the network 102 may include one or more devices such as computers, servers, routers, modems, switches, hubs, or any other networking equipment.

In further embodiments of the property inspection system 100, the data collection module 101 may be handled or operated by a person. The data collection module 101 may also be affixed to a locally or remotely controlled device. The data collection module 101 may also be affixed to a device that crawls or rolls along a surface; or a flying device, such as a unmanned aerial vehicle ("UAV"), airplane or helicopter. In some embodiments, the helicopter may be a multicopter with two or more rotors. The data collection module 101 may also be affixed to a projectile, balloon or satellite.

Figure 2:
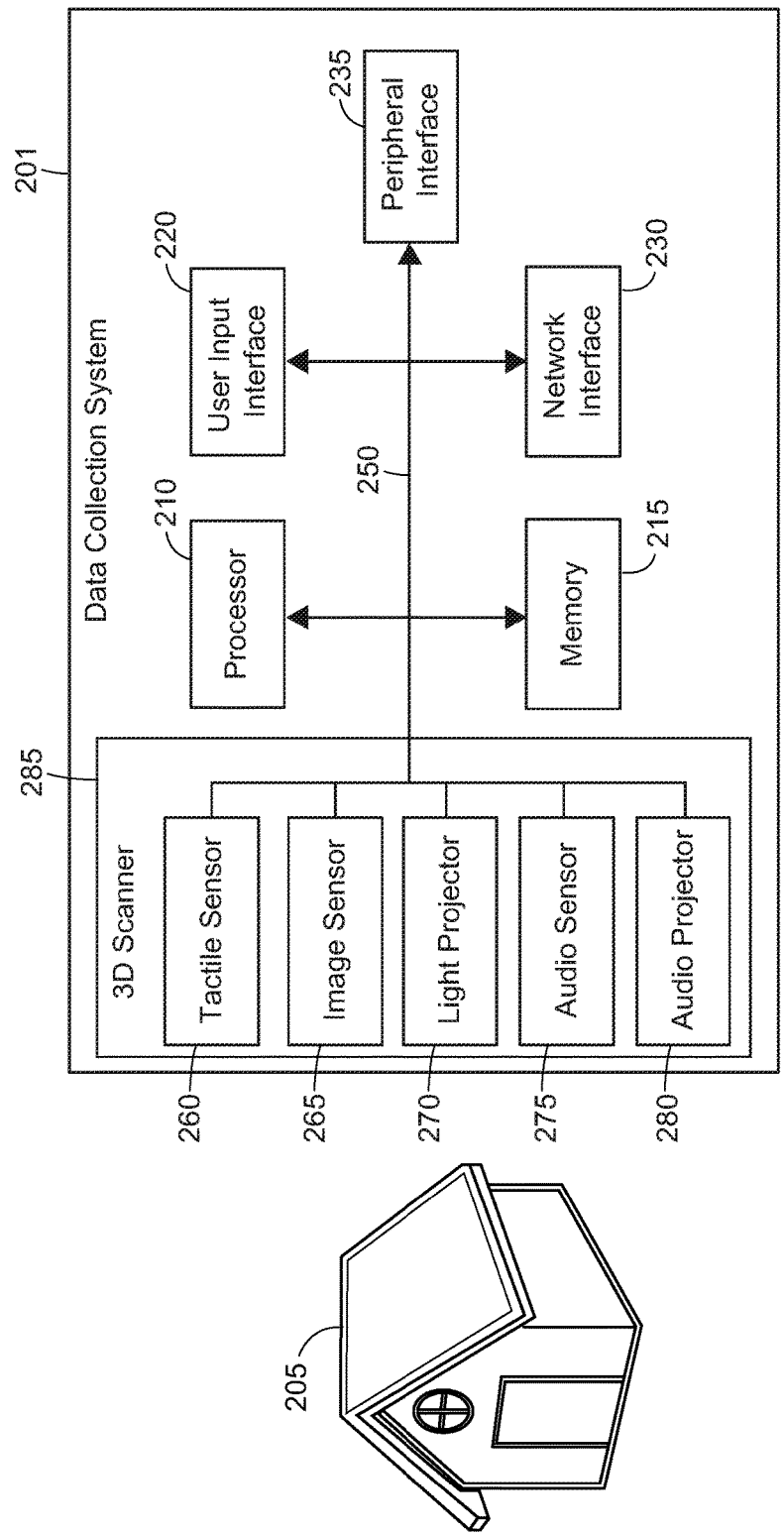
FIG. 2 illustrates a block diagram of a data collection system according to an embodiment of the present disclosure.

FIG. 2 illustrates a block diagram of a data collection system 201 according to an embodiment of the present disclosure. The data collection system 201 is used to scan the structure 205. The structure 205 may be any of the aforementioned structure types, such as a building, boat, vehicle, or aircraft. The data collection system 201 includes a processor 210, a memory 215, a user input interface 220, a network interface 230, a peripheral interface 235, a system bus 250, and a 3D scanner 285. The 3D scanner 285 includes a tactile sensor 260, an image sensor 265, a light projector 270, an audio sensor 275, and an audio projector 280. In alternative embodiments, the 3D scanner 285 of the data collection system 201 may include only one of, or some subset of: the tactile sensor 260, the image sensor 265, the light projector 270, the audio sensor 275, and the audio projector 280. Some embodiments may also have multiple tactile sensors, multiple image sensors, multiple light projectors, multiple audio sensors, or multiple audio projectors.

In certain embodiments of the memory 215 of the data collection system 201, the memory 215 may include volatile and/or non-volatile memory and may be removable or non-removable memory. For example, the memory 215 may include computer storage media in the form of random access memory (RAM), read only memory (ROM), EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information. The network interface 230 may include an antenna, a port for wired connection, or both.

In some embodiments of the peripheral interface 235 of the data collection system 201, the peripheral interface 235 may be a serial interface such as a Universal Serial Bus (USB) interface. In other embodiments the peripheral interface 235 may be a wireless interface for establishing wireless connection with another device. For example, in some embodiments the peripheral interface 235 may be a short range wireless interface compliant with standards such as Bluetooth (operating in the 2400-2480 MHz frequency band) or Near Field Communication (operating in the 13.56 MHz frequency band).

In the preferred embodiments of the 3D scanner 285 of the data collection system 201, the 3D scanner 285 is a non-contact 3D scanner, which may be active (where the 3D scanner 285 emits radiation and detects the reflection of the radiation off of an object) or passive (where the 3D scanner 285 detects radiation that it did not emit). In other embodiments the 3D scanner 285 may be a contact 3D scanner that scans an object by coming into physical contact with the object. The 3D scanner may be a time-of-flight 3D scanner, a triangulation 3D scanner, a conoscopic 3D scanner, volumetric 3D scanner, a structured light 3D scanner, or a modulated light 3D scanner. The 3D scanner may use light detection and ranging (LIDAR), light field, stereoscopic, multi-camera, laser scanning, ultrasonic, x-ray, distance range system (laser or acoustic) technology, or some combination thereof. In typical embodiments, the 3D scanner 285 includes a controller, microcontroller or processor for controlling the 3D scanner 285 and included components. Furthermore, in certain embodiments the 3D scanner includes internal memory.

In some embodiments of the 3D scanner 285 of the data collection system 201, the image sensor 265 may include any of a number of photosensor, photodiode, photomultiplier, or image sensor types, including charge-coupled-devices (CCD), complementary metal-oxide-semiconductors (CMOS), or some combination thereof. In some instances the image sensor 265 may be a single-camera setup. In other instances, the image sensor 365 may be a multi-camera setup. The light projector 270 may include one or more light sources and may project light in the frequency of either visible or invisible light (including infrared light and ultraviolet light). The light projector 270 may also project directional light such as a laser light. The light projector 270 may include, but is not limited to, LED, incandescent, fluorescent, high intensity discharge lamp, or laser light sources. The audio sensor may include any of a number of audio sensor or microphone types. For example, the audio sensor may include one or more condenser microphones, dynamic microphones, piezoelectric microphones, fiber optic microphones, laser microphones, or MEMS microphones.

The data collection system 201 may be held and operated by a person. The data collection system 201 may also be affixed to a remotely controlled device, such as a radio controlled device; a flying device; a device that rolls, drives, crawls, climbs or drives; a mechanical apparatus affixed to or near the structure 205; or a satellite. The processor 210, the memory 215, the user input interface 220, the network interface 230, the peripheral interface 235, and the 3D scanner 285 are each communicatively connected to the system bus 250. In the preferred embodiment, the tactile sensor 260, the image sensor 265, the light projector 270, the audio sensor 275, and the audio projector 280 are also communicatively connected to the system bus 250. In certain embodiments, the tactile sensor 260, the image sensor 265, the light projector 270, the audio sensor 275, and the audio projector 280 communicate over a bus internal to the 3D scanner and are controlled by the 3D scanner.

In some embodiments of the data collection system 201, all or some of the elements in the data collection system 201 may be in contact with or close proximity to the structure 205. In other embodiments of the invention, all or some of the aforementioned elements may be remotely located in relation to the structure 205 (for example, and as discussed later, the data collection system 201 may be affixed, in whole or in part, to a satellite in orbit). The processor 210 is configured to fetch and execute instructions stored in the memory 215. The memory 215 is configured to store data such as operating system data or program data. The user input interface 220 is configured to receive user input and to transmit data representing the user input over the system bus 250. The peripheral interface 235 is configured to communicatively connect to a peripheral device such as a computer. The network interface 230 is configured to communicatively connect to a network, such as the network 102 shown in FIG. 1b, and wirelessly receive or transmit data using the network. In alternative embodiments, the network interface 230 may receive and transmit data using a wired connection, such as Ethernet.

The 3D scanner 285 is configured to receive control commands over the system bus 250 and scan an object such as the structure 205 to detect 3D characteristics of the scanned object. The 3D scanner 285 is further configured to transmit data representing a 3D data point, a point cloud or a 3D model ("3D data") relating to the scanned object over the system bus 250. The 3D scanner is further configured to use any of the tactile sensor 260, the image sensor 265, the light projector 270, the audio projector 270, or the audio projector 280 to generate and transmit the 3D data. The tactile sensor 260 is configured to capture sensory information associated with a surface of the structure 205 ("tactile data"), such as shapes and features or topography of the surface, and transmit the tactile data over the system bus 250. The image sensor 265 is configured to capture an image of the structure 205 and transmit data representing the image ("image data") over the system bus 250. In certain embodiments, the image sensor may receive visible light, invisible light (such as infrared or ultraviolet), or radiation in other parts of the electromagnetic spectrum (radio waves, microwaves, x-rays, gamma rays, etc.). In some embodiments, for example, subsurface features may be detected using radar. The transmitted image data may represent a thermal, color, infrared, or panchromatic image. The light projector 270 is configured to receive control commands over the system bus 250 from the 3D scanner 285 or the processor 210, and is further configured to project light in the direction of the structure 205. The audio sensor 275 is configured to receive an audio signal or sound waves reflected off of the structure 205 and transmit data representing the audio signal ("audio data") over the system bus 250. The audio projector 280 is configured to receive control commands over the system bus 250 or from the 3D scanner 285 and project a sound or audio signal in the direction of the structure 205.

In operation of the 3D scanner 285 of data collection system 201, the network interface 250 receives data representing a command to collect 3D information associated with the structure 205 ("3D capture command"). The network interface 250 transmits the 3D capture command over the system bus 250 to the processor 210, where the 3D capture command data is received. The processor 210 then transmits, over the system bus 250, a signal ("3D capture signal") instructing the 3D scanner 285 to detect 3D characteristics associated with an object. The 3D scanner 285 scans the structure 205 and generates data representing 3D characteristics of the structure 205 ("3D data") corresponding to the collected 3D information. More particularly, in one embodiment the 3D scanner 285 projects a light pattern onto the structure 205. The 3D scanner 285 then records the structure 205 and the projected light pattern. The 3D scanner 285 may then alter the projected light pattern or the area of the structure 205 on which the light pattern is projected. The 3D scanner 285 then records, for a second time, the structure 205 and projected light pattern. This process may be continuously repeated until a sufficient portion of the structure 205 has been scanned.

In further operation of the 3D scanner 285, the 3D scanner 285 analyzes the deformations associated with each of the recorded light patterns to identify coordinate sets associated with the structure 205. Each coordinate set includes vertical, horizontal, and depth distance measurements (relative to the 3D scanner 285) of a particular point on the surface of the structure 205. The 3D scanner 285 generates 3D data points representing each of the coordinate sets associated with the scanned points on the surface of the structure 205. In some embodiments (particularly in embodiments where the 3D scanner moves or uses sensors in multiple locations or positions), the 3D scanner 285 may normalize the coordinates for all of the collected 3D data points so that the 3D data points share a common coordinate system. In alternative embodiments, the coordinates may be normalized by a processor external to the 3D scanner 285. In any event, the 3D scanner 285 then stores a point cloud, constructed from the 3D data points, to memory 215. The processor 210 operates to transmit the 3D data (i.e., the point cloud) to the network interface 230, where the 3D data is transmitted over a network such as the network 102 shown in FIG. 1b. In certain embodiments, the 3D data may represent a 3D model that was constructed by the processor 210 or the 3D scanner 285.

In alternative embodiments of the 3D scanner 285, the 3D scanner may be a time-of-flight 3D scanner where the round trip time of a laser is identified in order to identify the distance to a particular point on the structure 205. The 3D scanner 285 may also be any type of triangulation 3D scanner that uses ordinary light or laser light. Furthermore, in some embodiments the 3D scanner 285 may use any one of or a combination of the tactile sensor 260, the image sensor 265, the light projector 270, the audio sensor 275, or the audio projector 280 in generating the 3D data.

In operation of the tactile sensor 260 of the 3D scanner 285, the tactile sensor 260 receives a signal from the 3D scanner 285 instructing the tactile sensor 260 to detect topographical features associated with a surface ("tactile capture signal"). The tactile sensor 260 receives the tactile capture signal and the tactile sensor 260 is exposed to a surface associated with the structure 205. The tactile sensor 260 generates tactile data representing at least some of the shapes and features of the surface that the tactile sensor 260 was exposed to. The 3D scanner 285 then uses the tactile data to generate 3D data. Alternatively, the tactile sensor 260 may transmit the tactile data over the system bus 250 to the memory 215 where the tactile data is stored.

In some embodiments of the tactile sensor 260 of the data collection system 201, the tactile sensor 260 may include, or be used with, a pad, mat, stamp, or surface that is depressed onto a surface associated with the structure 205. The tactile sensor 260, may then be used to detect the imprint made on the pad. Furthermore, the pad may have an adhesive surface so that any objects on the surface of the structure 205 (such as a shingle) stick to the pad. The tactile sensor 260 may then detect the resistive force exerted by the object as the pad is pulled away from the structure 205. In further embodiments, the tactile sensor 260 may use a roller that is run across a surface of the structure 205, wherein the shapes and features of the surface are temporarily imprinted on the roller and the tactile sensor 260 detects the shapes and features that have been temporarily imprinted on the roller.

In operation of the image sensor 265 of the 3D scanner 285, the image sensor 265 receives a signal ("image capture signal") from the 3D scanner 285 instructing the image sensor 265 to capture reflected light or to capture an image. The image sensor 265 receives the image capture signal and the image sensor 265 is exposed to light reflected off of the structure 205. The image sensor 265 generates image data representing at least part of an image of the structure 205, wherein the image corresponds to the light that the image sensor 265 was exposed to. The 3D scanner 285 then uses the image data to generate 3D data. Alternatively, the image data may be transmitted over the system bus 250 to the memory 215 where the image data is stored. Furthermore, the 3D scanner 285 may also use image data corresponding to multiple previously captured images to generate the 3D data.

In some embodiments, the image sensor 265 may be utilized to capture 2D images. In some embodiments the 3D scanner 285 may use the image sensor 265 to capture 2D images in order to supplement the 3D data captured by the 3D scanner 285. In other embodiments, the data collection system 201 may use the image sensor 265 to capture 2D images independently of the 3D scanner 285. The 2D image data may be transmitted to the memory 215 to be stored. The 2D image data may also be transmitted, via the network interface 230, to a data analysis module such as the data analysis module 103, where the 2D image data, or combination 2D-3D image data, may analyzed to estimate the condition of the structure 205.

In some embodiments of the image sensor 265, the image sensor 265 may be used to detect thermal characteristics associated with the structure 205 in addition to visual characteristics associated with the structure 205 (capturing infrared light, for example). Furthermore, in some embodiments the light reflected off of the structure 205 may originate from the light projector 270, while in other embodiments the light may originate elsewhere. In the former case, the processor 210 or the 3D scanner 285 operates to transmit a command instructing the light projector 270 to generate light. The light projector 270 receives the command to generate light and projects light in the direction of the structure 205. The light may be visible light, such as laser light or ordinary light emitted from an HID lamp; or invisible light, such as infrared light or ultraviolet light. In certain embodiments, the light projector 370 may also be configured to emit radiation in other frequencies of the electromagnetic spectrum (e.g., radio waves, microwaves, terahertz radiation, x-rays, or gamma rays). For example, the light projector 370 may emit radio waves. The radio waves may reflect off the structure 205 and may be detected by an antenna (not shown) communicatively coupled to the data collection system 201. In such an embodiment, the light projector and antenna may operate as a radar system, allowing the data collection system 201 to, for example, scan a subsurface associated with the structure 205. In one embodiment, for example, the data collection system 201 may scan the subsurface associated with shingles, enabling a data analysis module to determine if the subsurface of the shingles are damaged.

In operation of the audio sensor 275 of the 3D scanner 285, the audio sensor 275 receives a signal from the 3D scanner 285 instructing the audio sensor 275 to detect audio or sound waves ("audio capture signal"). The audio sensor 275 receives the audio capture signal and the audio sensor 275 is exposed to one or more audio signals or sound waves reflected off of the structure 205. The audio sensor 275 generates audio data representing at least part of one of the audio signals that the audio sensor 275 was exposed to. The 3D scanner 285 then uses the audio data to generate 3D data. Alternatively, the audio data may then be transmitted over the system bus 250 from the audio sensor 275 to the memory 215 where the audio data is stored.

In some embodiments of the audio sensor 275 of the data collection system 201, the audio signals or sound waves received at the audio sensor 275 may originate from the audio projector 280, while in other embodiments the audio signals may originate elsewhere. In the former case, the processor 210 operates to transmit a command instructing the audio projector 280 to generate audio. The audio projector 280 receives the command to generate audio and emits one or more sound waves or audio signals in the direction of the structure 205. In certain embodiments the audio sensor 275 and the audio projector 280 may operate as a sonar system, allowing the data collection system 201 to, for example, scan a subsurface associated with the structure 205. In one embodiment, for example, the data collection system 201 may scan the subsurface associated with shingles, enabling a data analysis module to determine if the subsurface of the shingles are damaged.

In alternative embodiments of the data collection system 201, the image capture signal, the audio capture signal, or the tactile capture signal may be received by from the processor 210, wherein the respective signal was generated in response to a capture command received by the processor 210 from the peripheral interface 235, the network interface 230, or the input interface 220. Likewise, the processor 210 may also operate to transmit the image data, audio data, tactile data, or 3D data to the network interface 230 or the peripheral interface 235 to be transmitted to another device or system.

In further embodiments of the data collection system 201, the data collection system 201 may include a chemical spray device, or may be used in conjunction with a chemical spray device, wherein the chemical spray device sprays a chemical onto a surface of the structure 205. The chemical may then be detected in order to help generate the image data or tactile data. In such an embodiment, the data collection system 201 may include or may be used in conjunction with a chemical detection sensor. In some embodiments, the presence of the chemical may also be detected using the image sensor 265. For example, a visually distinct or luminescent chemical (such as a phosphorescent or fluorescent chemical) may be sprayed on the structure 205. The image sensor 265 may then be used to detect the presence and extent of luminescence on the structure 205. A black light may also be used in conjunction with the process of detecting the chemical. The degree of luminescence present on the structure 205 may be used to determine topographical features associated with the structure 205 and may be used by the 3D scanner in generating 3D data. For example, the degree of luminescence may indicate pooling or seeping at certain locations on the surface of the structure. Detecting the luminescent chemical may also reveal run-off or drainage patterns, which may indicate an uneven surface or a dent on the surface.

In further alternative embodiments of the data collection system 201, the data collection system 201 may be configured to implement a data analysis method wherein the processor 210 accesses one or more of the image data, the audio data, the tactile data, or the 3D data on the memory 215 for analysis. The processor 210 may further operate to estimate the condition of the structure 205 based on said analysis.

Figure 3:
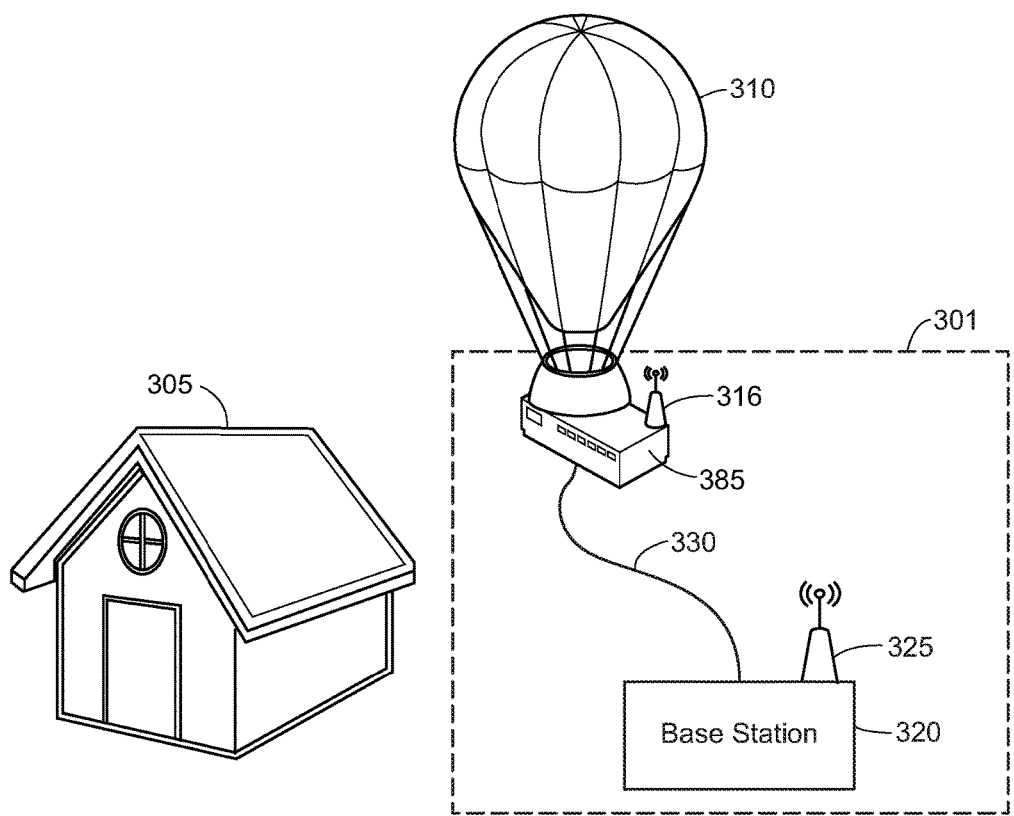
FIG. 3 illustrates a block diagram of a data collection system according to an embodiment of the present disclosure.

FIG. 3 illustrates a block diagram of a data collection system 301 according to an embodiment of the present disclosure. The data collection system 301 is configured to scan the structure 305. The data collection system 301 includes a 3D scanner 385, a flying device 310, a base station 320, an antenna 325, and a tether 330. The 3D scanner 385 includes an antenna 316. The flying device 310 may be a balloon, airplane, helicopter, projectile, rocket, or any other device capable of flight, levitation, or gliding.

In the preferred embodiment, the 3D scanner 385 is similar to the 3D scanner 285 and may also include one or more of: a tactile sensor similar to the tactile sensor 260, an image sensor similar to the image sensor 265, a light projector similar to the light projector 270, an audio sensor similar to the audio sensor 275, or an audio projector similar to the audio projector 280. The base station 320 may include one or more of: a processor similar to the process 210, a memory similar to the memory 215, a peripheral interface similar to the peripheral interface 230, a user input interface similar to the user input interface 220, or a transmitter similar to the transmitter 235.

In the data collection system 301, the 3D scanner 385 is affixed to the flying device 310. In the data collection system 301, the 3D scanner 385 is tethered to the base station 320. The antenna 316 of the 3D scanner 385 is in communication with the antenna 325 of the base station 320.

In operation of the data collection system 301, the flying device 310 is used to position the 3D scanner 385 at an elevation higher than at least part of the structure 305. The tether 330 functions to keep the flying device 310 within the vicinity of the base station 320 by tethering the flying device 310 to the base station 320. In some embodiments, the tether 330 may provide power to the flying device 310. The tether may also provide a communication channel between the flying device 310 and the base station 320 (and may replace the antennas 316 and 325 in certain embodiments). When the 3D scanner 385 has reached the desired elevation, the 3D scanner 385 collects information associated with the structure 305. In the preferred embodiment, the 3D scanner 385 scans the structure 305 and generates 3D data (e.g., 3D data points, a point cloud, or a 3D model). In some embodiments the 3D scanner 385 may collect image information, audio information, or tactile information as discussed with regard to the data collection system 201. The 3D scanner 385 then uses the antenna 316 to transmit the collected information to the antenna 325 of the base station 320. The base station 320 then transmits the collected information over a network such as network 102 shown in FIG. 1*b*.

In alternative embodiments of the data collection system 301, the base station 320 may be affixed to the flying device 310 along with the 3D scanner 285 and the tether 330 may instead tether the data collection system 301 to an anchoring device or apparatus. In such an embodiment, the components of the data collection system 301 may communicate over a system bus such as the system bus 250 discussed with regard to FIG. 2.

In further embodiments of the data collection system 301, the flying device 310 may operate to bring the 3D scanner 385 in contact with the structure 305, or may drop the 3D scanner 385 onto the structure 305. In some embodiments, the flying device 310 may operate autonomously. The flying device 310 may also be controlled wirelessly by a remote device such as a radio control device. Furthermore, in certain embodiments the 3D scanner 385 may be free of a connection to the tether 330. In some embodiments the 3D scanner 385 may be held and operated by a person, while in others the 3D scanner 385 may be affixed to a mechanical apparatus located on or near the structure 305.

Figure 4:
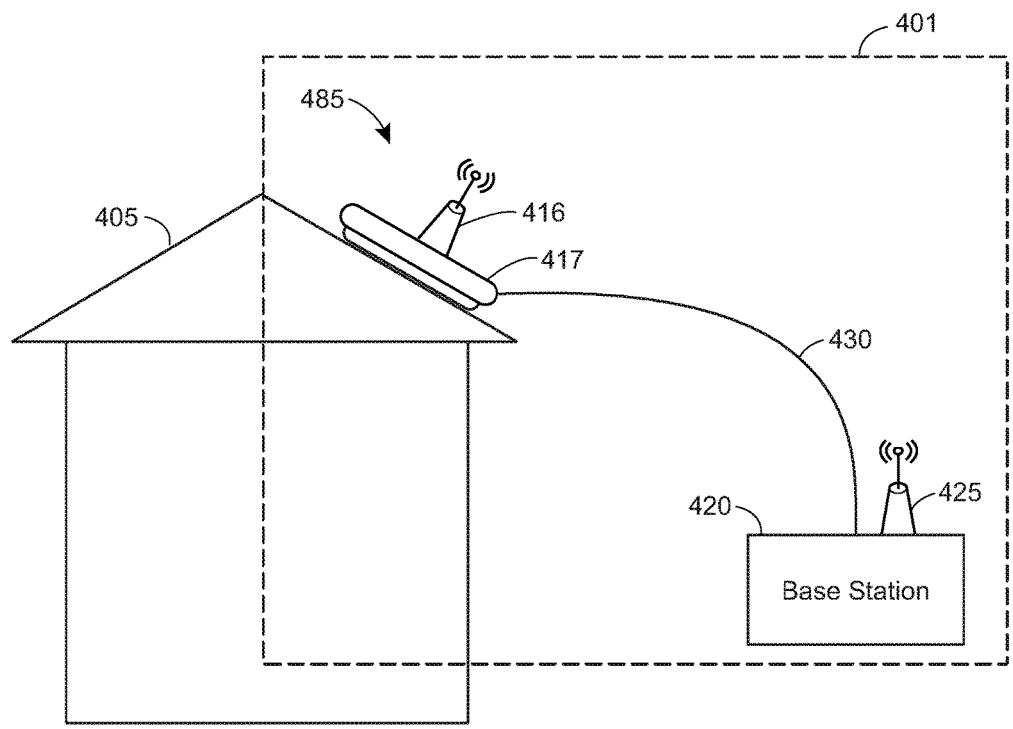
FIG. 4 illustrates a block diagram of a data collection system according to an embodiment of the present disclosure.

FIG. 4 illustrates a block diagram of a data collection system 401 according to an embodiment of the present disclosure. The data collection system 401 includes a 3D scanner 485, a base station 420, and a tether 430. The 3D scanner 485 includes an antenna 416 and a roller 417. The base station 420 includes an antenna 425.

The 3D scanner 485 may also include one or more of: a tactile sensor similar to the tactile sensor 260, an image sensor similar to the image sensor 265, a light projector similar to the light projector 270, an audio sensor similar to the audio sensor 275, an audio projector similar to the audio projector 280, or a 3D scanner similar to the 3D scanner 285. The base station 420 may include one or more of: a processor similar to the process 210, a memory similar to the memory 215, a peripheral interface similar to the peripheral interface 230, a user input interface similar to the user input interface 220, or a transmitter similar to the transmitter 235.

In the data collection system 401, the roller 417 of the 3D scanner 485 comes into contact with a surface of the structure 405. The 3D scanner 485 is physically connected to the base station 420 by the tether 430. The antenna 416 of the 3D scanner 485 is in communication with the antenna 425 of the base station 420.

In operation of the data collection system 401 of the data collection system 401, the 3D scanner 485 is deployed on a surface associated with the structure 405. The roller 417 comes into contact with the surface and rolls as the 3D scanner 485 moves. The roller 417 experiences a temporary imprint as it rolls, reflecting the shapes and features of the surface that it is rolling across. Sensors internal or external to the roller (such as the tactile sensor 260 of FIG. 2) detect the imprinted texture. The 3D scanner 485 generates tactile data representing the imprinted texture, The 3D scanner uses the tactile data to generate 3D data and uses the antenna 416 to transmit the 3D data to the antenna 425 of the base station 420. The base station 420 may then transmit the 3D data over a network such as the network 102 shown in FIG. 1*b*.

In further embodiments of the 3D scanner 485, the 3D scanner 485 may have mechanical feelers for contacting a surface associated with the structure 405. The mechanical feelers may pull on an object associated with the surface (such as shingles on a roof) by gripping the object between opposable feelers in order to detect how strongly adhered to the surface the object is. Alternatively, the 3D scanner 485 may deploy a mechanical feeler with an adhesive surface that detects how strongly an object is adhered to the surface by applying the adhesive surface of the mechanical feeler to the object, pulling the mechanical feeler away from the object, and detecting the resistive force associated with the object. Furthermore, the 3D scanner 485 may deploy a mechanical feeler to physically manipulate the surface or an object on the surface (by tapping, pulling, or scraping, for example) and using an audio sensor (such as the audio sensor 275, for example) to detect the audio response to the physical manipulation. The audio response may be analyzed (by the data analysis module 103 shown in FIG. 1*b*, for example) and used in determining the condition of the structure 405. In some embodiments, either or both of the data collection system 401 and the 3D scanner 485 may be unconnected to the tether 430.

In another embodiment of the 3D scanner 485, the 3D scanner 485 may include a pad or a stamp instead of or in addition to the roller 417. The 3D scanner 485 may depress the stamp onto a surface of the structure 405. The features and shapes of the surface cause an imprint on the stamp and the sensing device detects the imprint using a tactile sensor such as the tactile sensor 260 shown in FIG. 2. As discussed previously with respect to the data collection system 201 shown in FIG. 2, the stamp or pad may also have an adhesive surface causing objects on the surface of the structure 405 to stick to the pad. The 3D scanner 485 may then detect the resistive force exerted by an object when the stamp or pad is pulled away from the surface of the structure 405.

In an alternative embodiment of the data collection system 401, the entire data collection system 401 may be affixed to or included in the 3D scanner 485. In such an embodiment, the tether 430 may instead tether the 3D scanner 485 to an anchoring device or apparatus on or near the ground, the structure 405, or some other point of attachment. In a further embodiment, the 3D scanner 485 may be controlled by a device remotely located relative to the 3D scanner 485. In particular, the 3D scanner 485 may be wirelessly controlled (e.g., via radio frequency by a radio control device). In other embodiments the 3D scanner 485 may operate autonomously.

Figure 5:
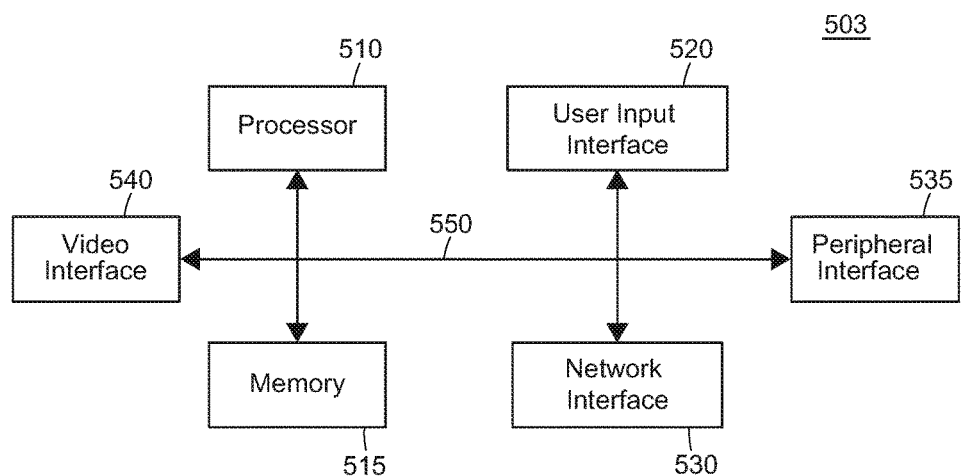
FIG. 5 illustrates a block diagram of a data analysis system according to an embodiment of the present disclosure.

FIG. 5 illustrates a block diagram of a data analysis system 503 according to an embodiment of the present disclosure. The data analysis system 503 includes a processor 510, a memory 515, a user input interface 520, a network interface 535, a peripheral interface 535, a video interface 540, and a system bus 550. The processor 510, memory 515, user input interface 520, network interface 535, peripheral interface 535, and video interface 540 are each communicatively connected to the system bus 550. The memory 515 may be any type of memory similar to memory 215. Likewise, the processor 510 may be any processor similar to the processor 210, the network interface 530 may be any network interface similar to the network interface 230, the peripheral interface 535 may be any peripheral interface similar to the peripheral interface 235, and the user input interface 520 may be any user input interface similar to the user input interface 220. The video interface 540 is configured to communicate over the system bus 540 and transmit video signals to a display device such as a monitor.

In operation of the data analysis system 503, the network interface 535 receives 3D data points corresponding to a structure such as the structure 205 shown in FIG. 2. The network interface 535 transmits the received data over the system bus 550 to the memory 515. The processor 510 accesses the memory 515 to generate a first 3D model of the structure based on the 3D data points, wherein the edges and vertices associated with the model are derived from the 3D data points. The processor 510 may then make one or more comparisons between the first 3D model and one or more second models. The second models may represent previously received data relating to the same structure, or they may represent previously received data relating to similar structures. Alternatively, the second models may have been created specifically for the purpose of estimating the condition of a structure and may not relate to any actual physical structure. Based on the one or more comparisons, the processor 510 generates an estimate of the condition of the structure. The estimate of the condition of the structure is saved to the memory 515. In some embodiments, network interface 535 may receive 2D image data or 2D-3D combination image data and may transmit the data to the memory 515. The processor 510 may identify features with the 2D images and/or 2D-3D combination images and may generate the estimate of the condition of the structure in accordance with the identified features.

In further operation of the data analysis system 503, the processor 510 may determine, based on the generated estimate, that the structure has been damaged. The processor 510 may then operate to calculate (based on the condition of the structure and data relating to costs such as cost of supplies, materials, components and labor) an estimated financial cost associated with the damage. The estimated financial cost is then saved to the memory 515. The video interface 540 may be used to display: the first 3D model, any of the one or more second models, the estimate of the condition of the structure, or the estimated financial cost.

In alternative embodiments of the data analysis system 503, the received data may also represent images, videos, sounds, thermal maps, pressure maps, or topographical maps, any of which may be displayed via the video interface 540. The received data may then be used to generate a 3D model. Alternatively, the received data may be compared to reference images, videos, sound, thermal maps, pressure maps, or topographical maps to estimate the condition of the structure.

Figure 6:
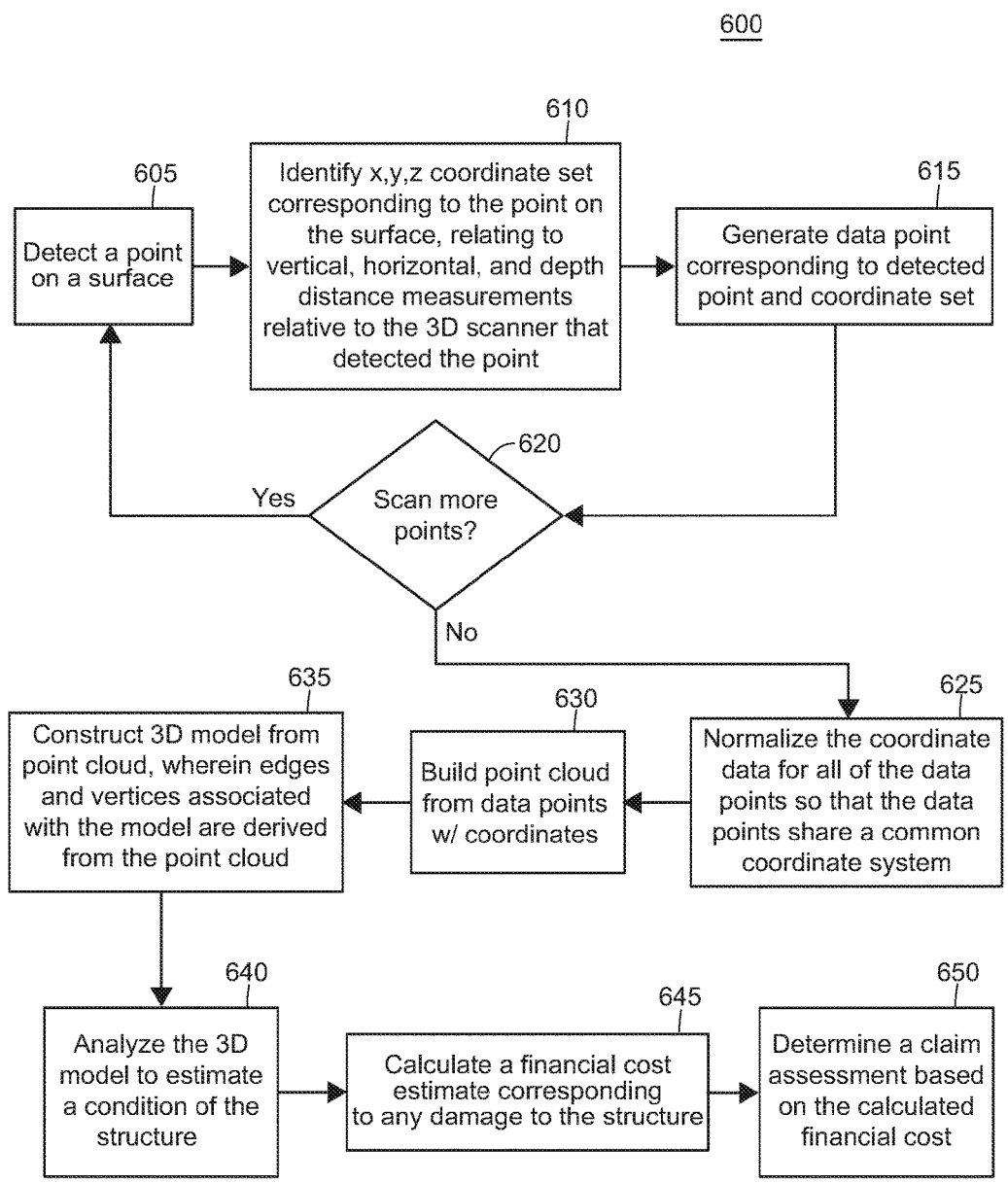
FIG. 6 illustrates a flow chart of an example method for inspecting and analyzing the condition of a structure.

FIG. 6 illustrates a flow chart of an example method 600 for inspecting and analyzing the condition of a structure. The method 600 may be implemented, in whole or in part, on one or more devices or systems such as those shown in the property inspection system 100 of FIG. 1, the data collection system 201 of FIG. 2, the data collection system 301 of FIG. 3, the data collection system 401 of FIG. 4, or the data analysis system 503 of FIG. 5. The method may be saved as a set of instructions, routines, programs, or modules on memory such as memory 215 of FIG. 2 or memory 515 of FIG. 5, and may be executed by a processor such as processor 210 of FIG. 2 or processor 510 of FIG. 5.

The method 600 begins when a 3D scanner scans a structure, such as the structure 205 shown in FIG. 2, structure 305 shown in FIG. 3, or structure 405 shown in FIG. 4, and detects a point on the surface of the structure (block 605). The structure may be any kind of building or structure. The structure may be, for example, a single-family home, townhome, condominium, apartment, storefront, or retail space, and the structure may be owned, leased, possessed, or occupied by an insurance policy holder. The structure may also be any of the structure types discussed regarding FIG. 1, such as a vehicle, boat, or aircraft. In such structures, the 3D scanner may be used to inspect the body panels, windows, frame, and other surfaces associated with the vehicle, boat, or aircraft. Next, the 3D scanner identifies a coordinate set corresponding to each detected point on the surface of the structure (block 610). The coordinate set relates to vertical, horizontal, and depth distance measurements relative to the 3D scanner that detected the point.

The 3D scanner then generates a 3D data point, corresponding to the detected point on the surface of the structure, that includes the corresponding coordinate data (block 615). The 3D data point may then be saved to memory. A decision is made thereafter to either stop scanning the structure or continue scanning the structure (block 620). If there is more surface area or more surface points to be scanned, the 3D scanner continues scanning the structure. Otherwise, the method 600 continues to block 625.

When it is determined that no further scanning is required, the method 600 activates the 3D scanner, or a processor such as the processor 210 of FIG. 2 or the processor 510 of FIG. 5, to normalize the coordinate data for all of the generated 3D data points so that the 3D data points share a common coordinate system (block 625). The normalized 3D data points may then be saved to memory. The 3D scanner, or a processor, operates to build a point cloud from the 3D data points (block 630). This may be done by sampling or filtering the 3D data points. Alternatively, all of the 3D data points may be used. In any event, the point cloud may then be saved to memory.

After the point cloud is saved, the 3D scanner or processor operates to construct a 3D model from the point cloud (block 635). The edges and vertices associated with the model are derived from the points in the point cloud. Any of a number of surface reconstruction algorithms may be used to generate the surface of the model. In certain embodiments the surface reconstruction may be skipped altogether and the raw point cloud may be subsequently used instead of the constructed 3D model.

Next, a processor such as the processor 210 of FIG. 2 or the processor 510 of FIG. 5 operates to analyze the 3D model (or point cloud) to estimate a condition of the structure (block 640). In some embodiments, this may include comparing the model to other models, wherein the other models relate to previously collected data corresponding to the same structure, or previously collected data corresponding to other structures. In the alternative, the other models may only exist for the purpose of analysis or estimation and may not correlate to any real structure.

Based on the estimated condition of the structure, a processor operates to calculate a financial cost estimate corresponding to any damage to the structure (block 645). In some embodiments, the financial cost estimate may correspond to the estimated cost for materials, labor, and other resources required to repair or refurbish the structure.

After calculating a financial cost estimate, a processor operates to determine a claim assessment (block 650). The claim assessment may then be saved to memory. In some embodiments the claim assessment may be sent to a third party associated with the structure, such as a client holding an insurance policy on the structure. In other embodiments the claim assessment may be sent to an insurance agent for evaluation.

Figure 7:
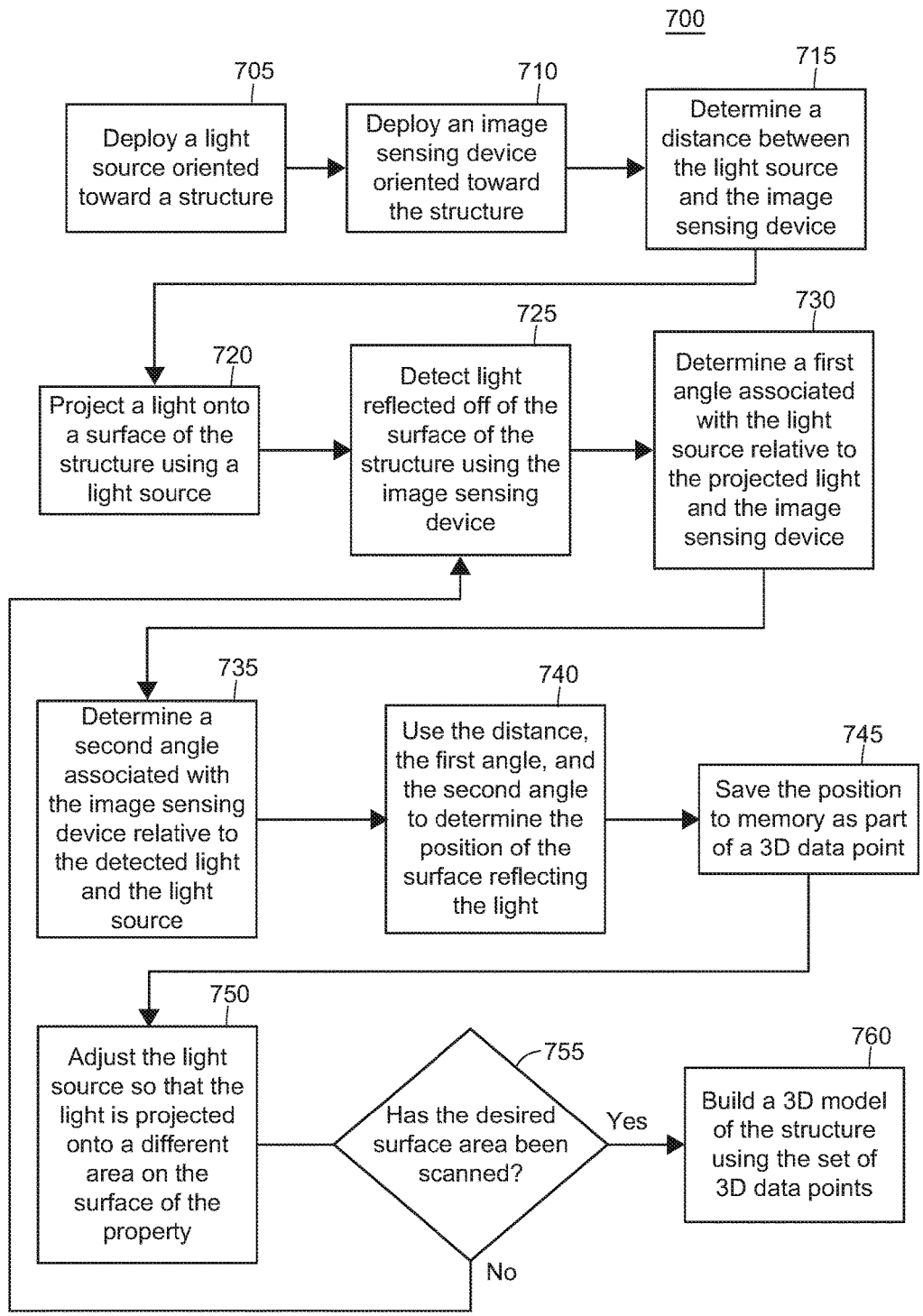
FIG. 7 illustrates a flow chart of an exemplary method for detecting a point on a surface using a 3D scanner.

FIG. 7 illustrates a flow chart of an exemplary method 700 for detecting a point on a surface using a 3D scanner. The method may be implemented by a 3D scanner, such as the 3D scanner 285 of FIG. 2 or the 3D scanner 385 of FIG. 3.

The method 700 begins when a light source is deployed oriented toward a structure such as structure 105, 205, 305, or 405 of FIG. 1, 2, 3, or 4, respectively (block 705). The light source may be a part of the 3D scanner, or it may be a separate device used in conjunction with the 3D scanner. The light source may be any type of light source, but in the preferred embodiment the light source is a laser that projects a dot or line. In other embodiments the light source may be a white light source that projects a pattern onto an object.

A photosensor or image sensing device, such as the image sensor 265 of FIG. 2, is then deployed oriented toward the structure (block 710). The image sensing device may be part of the 3D scanner, or it may be a separate device used in conjunction with the 3D scanner. In the preferred embodiment, the image sensing device is capable of detecting and processing laser light. After the image sensing device has been deployed, the distance between the light source and the image sensing device is determined (block 715).

The light source projects light onto a surface of the structure (block 720) and the image sensing device detects light reflected off of the surface of the structure (block 725). In order to identify the position of the surface reflecting the light, a first and second angle are determined (block 730 and block 735, respectively). The first angle includes the light source as an end point, the projected light beam or laser as a first side, and a line extending to the image sensing device as the second side of the angle. The second angle includes the image sensing device as an end point, the received light beam or laser as a first side, and a line extending to the light source as a second side of the angle. Finally, the position (including depth) of the surface reflecting the light is determined (block 740) using the distance discussed in relation to block 715, the first angle discussed in relation to block 730, and the second angle discussed in relation to block 735.

The position of the surface reflecting the light is saved to memory as coordinate data included in a 3D data point (block 745). The coordinate data may be relative to the 3D scanner, or it may be normalized so that is it is consistent with other saved 3D data points. After saving the coordinate data, the light source is adjusted so that the light is projected onto a different area on the surface of the property (block 750). A decision is then made to either continue scanning or stop scanning (block 755). If more of the structure needs to be scanned, the method returns to step 725 where the light from the adjusted light source is reflected off of the surface of the structure and detected. If the structure has been sufficiently scanned, the 3D scanner or a processor can begin the process of building a 3D model of the structure using the 3D data points.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Discussions herein referring to an "appraiser," "inspector," "adjuster," "claim representative" or the like are non-limiting. One skilled in the art will appreciate that any user associated with an insurance company or an insurance function may utilize one or more of the devices, systems, and methods disclosed in the foregoing description. One skilled in the art will further realize that any reference to a specific job title or role does not limit the disclosed devices, systems, or methods, or the type of user of said devices, systems, or methods.

Certain implementations are described herein as including logic or a number of components, modules, or mechanisms. Modules may constitute either software modules (e.g., code implemented on a tangible, non-transitory machine-readable medium such as RAM, ROM, flash memory of a computer, hard disk drive, optical disk drive, tape drive, etc.) or hardware modules (e.g., an integrated circuit, an application-specific integrated circuit (ASIC), a field programmable logic array (FPLA)/field-programmable gate array (FPGA), etc.). A hardware module is a tangible unit capable of performing certain operations and may be configured or arranged in a certain manner. In example implementations, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one implementation," "one embodiment," "an implementation," or "an embodiment" means that a particular element, feature, structure, or characteristic described in connection with the implementation is included in at least one implementation. The appearances of the phrase "in one implementation" or "in one embodiment" in various places in the specification are not necessarily all referring to the same implementation.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for inspecting a structure to estimate the condition of a structure through the disclosed principles herein. Thus, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A computer-implemented method of inspecting a structure, the method comprising:
projecting onto a surface of a structure a light pattern;
detecting, by one or more 3D scanners, deformations in the light pattern projected onto the surface of the structure, wherein detecting the deformations in the light pattern comprises positioning the one or more 3D scanners via an aerial device so that the one or more 3D scanners can detect the deformation in the light pattern;
generating, by the one or more 3D scanners, a 3D point cloud based on the detected deformation in the light pattern;
analyzing, by one or more processors, the generated 3D point cloud to identify one or more features of the surface of the structure;
generating, by the one or more processors, an estimate of a condition of the surface of the structure based on the identified one or more features; and
storing the generated estimate at one or more memories.

2. The method of claim 1, wherein positioning the one or more 3D scanners comprises: (i) positioning the one or more 3D scanners via an on-board control system of the aerial device configured for autonomous operation; (ii) positioning the one or more 3D scanners by wirelessly transmitting control commands to the aerial device; or (iii) positioning the one or more 3D scanners by transmitting from a base station via a tether control commands to the aerial device.

3. The method of claim 1, wherein detecting the deformations in the light pattern comprises positioning the one or more 3D scanners via a non-aerial device so that the one or more 3D scanners can detect the deformation in the light pattern.

4. The method of claim 3, wherein positioning the one or more 3D scanners comprises: (i) positioning the one or more 3D scanners via an on-board control system of the non-aerial device configured for autonomous operation; (ii) positioning the one or more 3D scanners by wirelessly transmitting control commands to the non-aerial device; or (iii) positioning the one or more 3D scanners by transmitting from a base station via a tether control commands to the non-aerial device.

5. The method of claim 1, further including causing the one or more processors to calculate a financial cost based on the estimate of the condition of the surface.

6. A system for inspecting a structure, the system comprising:
a first means for projecting onto a surface of a structure a light pattern;
a second means for detecting deformations in the light pattern projected onto the surface of the structure;
a third means for generating a 3D point cloud based on the detected deformation in the light pattern;
a fourth means for analyzing the generated 3D point cloud to identify one or more features of the surface of the structure;
a fifth means for generating an estimate of a condition of the surface of the structure based on the identified one or more features;
a sixth means for storing the generated estimate; and
a device that conveys the second means so that the second means can be positioned to detect the deformations in the light pattern, wherein the device is an aerial device.

7. The system of claim 6, wherein the device includes an on-board control system configured for autonomous operation.

8. The system of claim 6, further including a seventh means for transmitting to the device control commands for causing the device to position the second means so that the second means can detect the deformation in the light pattern.

9. The system of claim 6, further including a seventh means for calculating a financial cost based on the estimate of the condition of the surface.

10. A system for inspecting a structure, the system comprising:
(A) a projector for projecting onto a surface of a structure a light pattern;
(B) one or more 3D scanners configured to: (i) detect deformations in the light pattern projected onto the surface of the structure, and (ii) generate a 3D point cloud based on the detected deformation in the light pattern;

(C) a device that conveys the one or more 3D scanners so that the one or more 3D scanners can be positioned to detect the deformations in the light pattern, wherein the device is an aerial device;

(D) one or more processors configured to execute instructions that, when executed, cause the one or more processors to:
  (i) generate a 3D point cloud based on the detected deformation in the light pattern;
  (ii) analyze the generated 3D point cloud to identify one or more features of the surface of the structure;
  (iii) generate an estimate of a condition of the surface of the structure based on the identified one or more features; and
  (iv) store to a memory the generated estimate.

11. The system of claim 10, wherein the device includes an on-board control system configured for autonomous operation.

12. The system of claim 10, further including a tether physically connected to the device.

13. The system of claim 12, wherein the tether provides a communication channel to the device, wherein the device receives control commands for positioning the device via the tether.

* * * * *